(12) United States Patent
Jacob et al.

(10) Patent No.: US 6,517,538 B1
(45) Date of Patent: Feb. 11, 2003

(54) TEMPERATURE-CONTROLLED SNARE

(76) Inventors: Harold Jacob, 657 Central Ave., Cedarhurst, NY (US) 11516; Yoed Rabin, 657 Central Ave., Cedarhurst, NY (US) 11516

( * ) Notice: Subject to any disclaimer, the term of this patent is extended or adjusted under 35 U.S.C. 154(b) by 0 days.

(21) Appl. No.: 09/419,451

(22) Filed: Oct. 15, 1999

(51) Int. Cl.$^7$ ................................................ A61B 18/18
(52) U.S. Cl. ........................................ 606/47; 606/113
(58) Field of Search ............................ 606/48, 47, 45, 606/38, 49, 113, 31

(56) References Cited

U.S. PATENT DOCUMENTS

| | | | |
|---|---|---|---|
| 5,158,561 A | * 10/1992 | Rydell et al. | 606/113 |
| 5,769,847 A | * 6/1998 | Panesu et al. | 606/42 |
| 5,836,947 A | * 11/1998 | Fleischmann et al. | 606/47 |
| 6,050,995 A | * 4/2000 | Durgin | 606/47 |

* cited by examiner

Primary Examiner—Michael Peffley
Assistant Examiner—P J Vrettakos
(74) Attorney, Agent, or Firm—Bernard Malina; Malina & Wolson (57) ABSTRACT

An apparatus, method and kit are provided for removal of polyps, especially pursuant to colonoscopic surgery. The apparatus includes an endoscopic guide tube, a heating element, a power transmitting element traversing through the guide tube and communicating with the heating element, at least one temperature sensor for measuring temperature near the polyp, and optionally an external monitor for receiving temperature data from the sensor and then activating a power source for adjusting the temperature of the heating element in a controlled manner. An operator/physician can manually set the temperature range and temperature increase rate, but preferentially this is achieved automatically through a pre-programmed computer schedule.

16 Claims, 6 Drawing Sheets

TEMPERATURE-CONTROLLED SNARE

BACKGROUND OF THE INVENTION

1. Field of the Invention

The invention concerns an apparatus, method and kit for removal of polyps from internal organs, especially the colon, of a human body.

2. Related Art

Colonoscopic polypectomy is a very common endoscopic procedure (Gillespie et al., *GUT* 20:240, 1979; Panish, *Am J. Gastroenterol*, 71:315, 1979; Shinya and Wolff, *Ann Surg* 109:679, 1979; Knutson and Max, *Arch Surg*, 114:440, 1979). The purpose of endoscopic polypectomy is to remove polyps from the colon that are detected during colonoscopy or other screening procedures. Illustrative of this technology are the disclosures found in U.S. Pat. No. 4,905,691; U.S. Pat. No. 5,158,561; and U.S. Pat. No. 5,540,683. Polypectomy is performed by passing a stainless steel wire loop through the colonscope (known as a snare) and placing it around the polyp. The loop is tightened and electrical energy is applied to the snare. Electrical energy is then transmitted to the tissue and converts to heat. Water in the tissue thereby heats up causing cells to explode resulting in coagulation and a cutting effect, separating polyp from tissue. The snare is then closed manually by the endoscopic assistant or the physician completing the polypectomy process.

Routine endoscopic polypectomy has a very high success rate and a very low complication rate. However, when the physician is confronted with sessile or thick stalked polyps, the procedure of endoscopic polypectomy becomes more challenging. In these cases, the limitations of the present technique of endoscopic polypectomy become apparent. First, the force applied while closing of the snare is a highly subjective action of the surgeon, performed in a highly uncontrolled manner. Secondly, the rate of resection during the electrical coagulation is typically an overlooked parameter which may significantly affect success of the operation. There are currently no indicators to guide the physician as to how fast and under what force to close the snare. In the absence of such an indication, undesired complications may take place. These complications may include excessive bleeding where the resection process proceeds too rapidly and there is insufficient coagulation of the underlying blood vessels. Alternatively, perforation of the GI tract may occur when excessive energy is applied to the tissue. (Fruhmorgen, *Colonscopy*, Chapman and Hall, 1981).

Accordingly, it is an object of the present invention to provide an apparatus, kit and method for performing a polypectomy that avoids surgical complications such as excessive bleeding and/or perforation of the gastrointestinal tract.

SUMMARY OF THE INVENTION

We propose that a key parameter in avoiding complications of polypectomy is temperature control of cutting edges forming the snare. Temperature sensors are provided to the area of the snare near and/or along the cutting edge, to indicate and control the resection process. Information gathered in monitoring temperature of that area is used for controlling the electrical coagulation in the endoscopic polypectomy.

The current invention is superior over prior art in the sense that resection is performed in a controlled manner. More specifically, the snare temperature is set as the controlled parameter of resection. It is commonly accepted that resection is preferable only above some threshold temperature of the snare's cutting edge but that too high temperatures are highly likely to involve complications.

Temperature control is achieved by the application of temperature sensors. Two preferred embodiments of the present invention involve: (i) an open-loop control system, where the operator/physician controls the electrical power supplied to the snare, in order to maintain temperatures in some working temperature range; and (ii) a close-loop control system, where an independent automatic temperature controller is applied to maintain some desired and pre-specified temperature above the threshold temperature.

Based on the foregoing discoveries, we provide an apparatus for polyp removal which includes:

(i) an endoscopic guide tube;

(ii) a heating element;

(iii) a power transmitting element traversing through the guide tube and communicating with the heating element; and (iv) at least one temperature sensor for measuring temperature near the polyp.

Preferably present will be a temperature controlling element for receiving temperature information from the sensor and then signaling a power source for adjusting the temperature of the heating element. Another useful component is an electrical power/temperature sensor synchronization device for deactivating the applied electrical power during periods of temperature measurement.

A kit for polyp removal is also provided utilizing the aforementioned apparatus and including instructions accompanying the kit for deploying the apparatus. The instructions recite the following steps:

(A) providing an endoscopic apparatus which features (i) through (iv) as mentioned above;

(B) inserting the endoscopic guide tube into a human body;

(C) deploying the heating element to surround a polyp; and (D) energizing the heating element in a temperature controlled manner.

BRIEF DESCRIPTION OF THE DRAWING

Further objects, features and advantages of the present invention will become more readily apparent from consideration of the following drawing in which.

DETAILED DESCRIPTION OF THE INVENTION

Figure 1A:
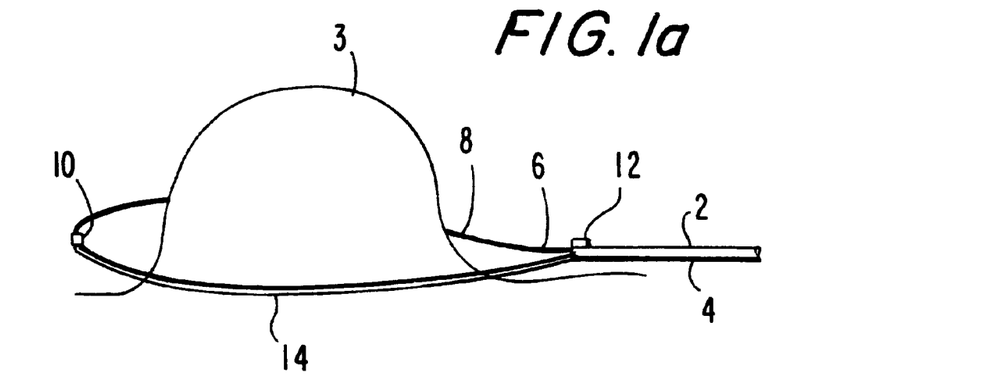
FIG. 1a schematically shows the temperature controlled snare of the present invention in the first stage of operation involving initial placement of snare loop around the polyp.
Figure 1B:
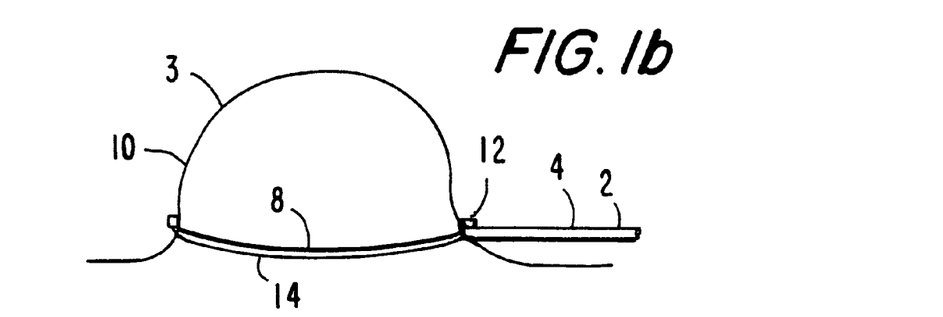
FIG. 1b schematically shows the temperature controlled snare of the present invention in the second stage of operation wherein the snare loop is tightened around the polyp.
Figure 1C:
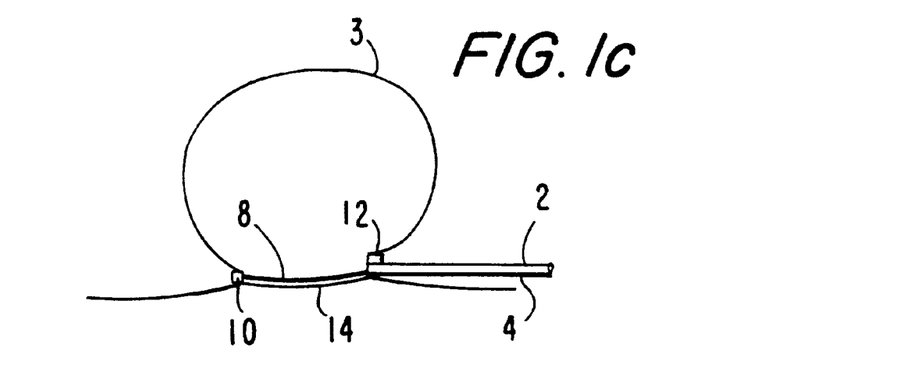
FIG. 1c schematically shows the temperature controlled snare of the present invention in the third stage of operation wherein excision of the polyp occurs.

FIGS. 1a through 1c schematically depict operation of a temperature-controlled snare. With reference to FIG. 1a, the first stage of operation involves identification of the desired tissue for resection (polyp). An endoscopic guide tube 2 is inserted down a colon of a human body. A power transmitting element 4 which traverses through the guide tube providing a heating element 6 in the form of a snare loop 8. Manipulation of the heating element 6 allows placement of the snare loop 8 around the polyp 3.

FIG. 1b illustrates a second stage of the operation. The snare loop 8 is tightened around the polyp 3 by pulling the snare loop through the endoscopic guide tube 2 in lassoo fashion by means of extendable thumb ring 21. A pair of temperature sensors 10, 12 are positioned at opposite ends of the loop 8 in contact with the polyp 3. As the sensors 10, 12 lightly press against the surface of the polyp 3, the temperature is measured and transmitted through sensor wires 14, which are electrically connected to sensors 10, 12, are bundled within and extend along the interior of endoscopic guide tube 2. Temperature information provided by the sensor wires 14 as electrical signals are then transmitted to an external monitor 16 and/or temperature controller 32.

Electrical coagulation is performed in a third step of the operation. FIG. 1c illustrates this step where the snare loop 8 closes around a base of the polyp 3. The electrical coagulation is driven by closing the electrical circuit between the snare loop 8 and a grounding pad 18 shown in FIG. 2. The temperature of the snare loop 8 elevates during and as a result of the applied electrical power. During the operation, temperatures are monitored by sensors 10, 12 at the respective far and near ends of the snare loop 8. Once the sensed temperatures reach a threshold value, the snare loop 8 is pulled into the endoscopic guide tube 2 to separate and cut the polyp 3 from its base. If temperature should exceed a specified upper temperature level, the electrical power is momentarily turned off, to prevent complications associated with excessive heating. This stage continues until complete resection of the polyp is achieved.

For purposes of this invention, the temperature is programmed over a range of about 50° C. to about 300° C., preferably from about 100° C. to about 200° C., optimally from about 150° C. to about 180° C. Rates of heating may vary from about 5° C. to about 50° C. per minute, preferably from about 10° C. to about 30° C. per minute.

Figures 2, 2A:
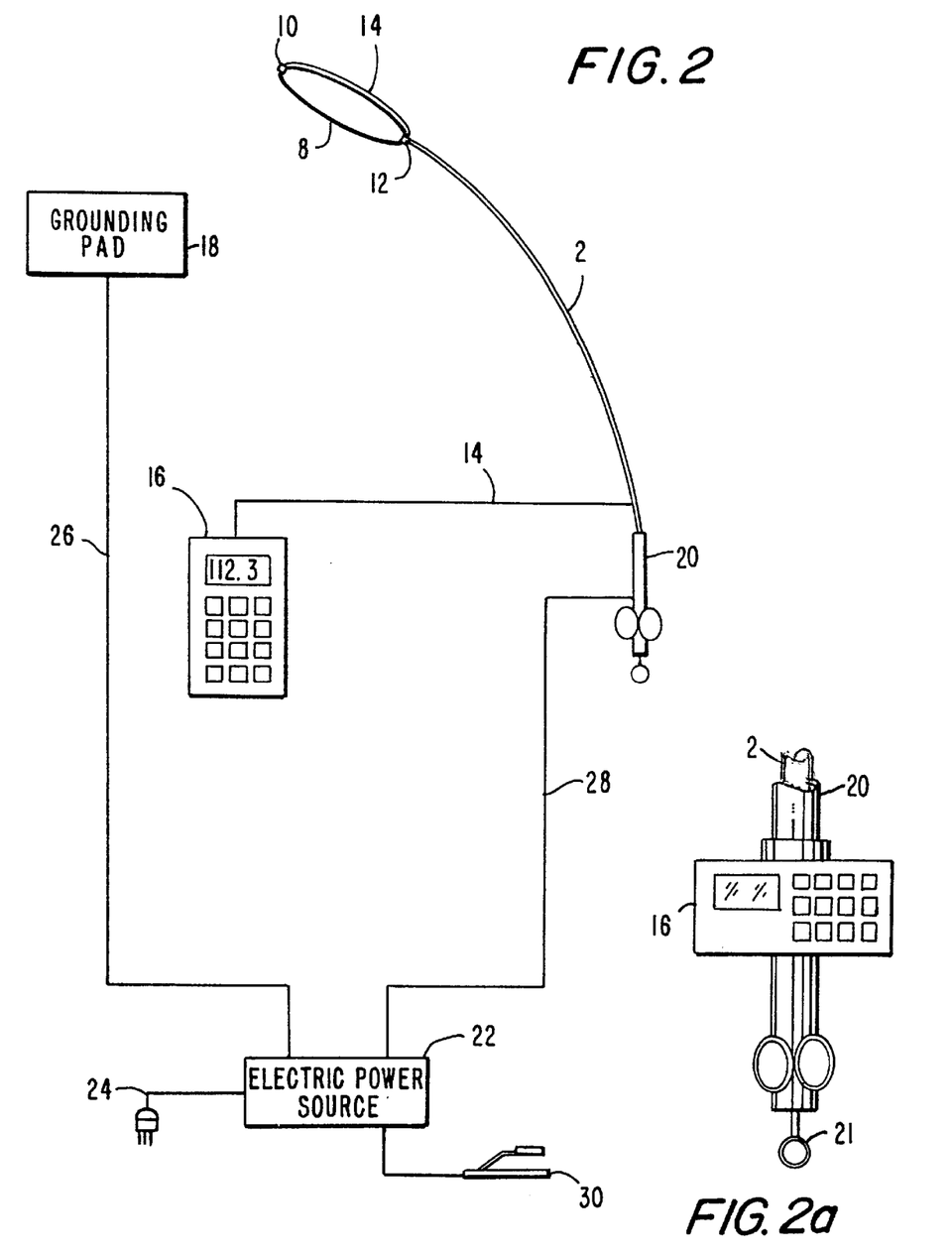
FIG. 2 depicts the temperature controlled snare of the present invention wherein the temperature-controlled snare operates in an open-loop configuration.
FIG. 2a shows the monitor of the present invention mounted on the handle assembly in another embodiment of the present invention.

FIG. 2 schematically illustrates a first embodiment wherein the temperature-controlled snare is in an open-loop configuration. A snare handle assembly 20 manipulates the snare loop 8 with a metallic cable (e.g., stainless-steel) which encloses a power transmitting element 4 and is itself guided within the endoscopic guide tube 2 (usually of plastic construction). The snare handle assembly 20 allows the metallic cable to move axially within the guide tube 2, close the snare loop 8 and perform a resection of the polyp.

Electrical coagulation is applied for resection by means of the following electrical system. An electrical power source 22 of the type routinely applied in operating rooms is utilized as an energy source. It is connected to an electrical network via a power cord 24. Power source 22 converts available electrical network voltage and current to a voltage and current suitable for electrocautery. Further elements of the circuit include grounding pad 18, which may be placed on an operating table (not shown) and brought in electrical contact with the patient; a grounding wire 26 which connects the pad 18 to the power source 22; an operation wire 28 which connects the power source 22 to the handle assembly 20; the metallic cable which is guided within the guide tube 2 and connects the handle assembly 4 to the snare loop; and the body of a patient which closes the electrical circuit between the snare loop and the grounded pad. Parameters for electrocautery are set at a front panel of the electric power source 22. An operation pedal 30 is connected to the power source 22 and closes the electric coagulation circuit whenever the operator/physician desires to apply heat to the snare loop 8.

The electrical current converts to heat at the snare loop 8 due to the electrical resistance of the biological tissues. This current converts into heat at the snare loop only, and not on the surface of the grounding pad as well, due to the relative small area of electrical contact, and hence high electrical resistance, between the snare and the patient's body, when compared to the large area of contact between the ground pad 18 and the patient's body. Thus, the surface electrical resistance of the snare loop 8 is much higher, whereby dramatically higher temperatures are generated along this area of contact.

In the application of electrical temperature sensors, such as thermocouples, RTD's, and thermistors, there is a danger of electrical shock to monitor 16, or high uncertainty in temperature readings, when applying high electrical power through the snare 8. One alternative means of protecting the monitor 16 is by connecting the sensor via an electrical amplifier/insulator (not shown) to the monitor. This amplifier/insulator may give unrealistic temperatures when power is applied, but exact values immediately thereafter. By this technique, the physician/surgeon operates the snare for short periods of time and reads the temperatures between every two consecutive electrical power applications.

Figure 3:
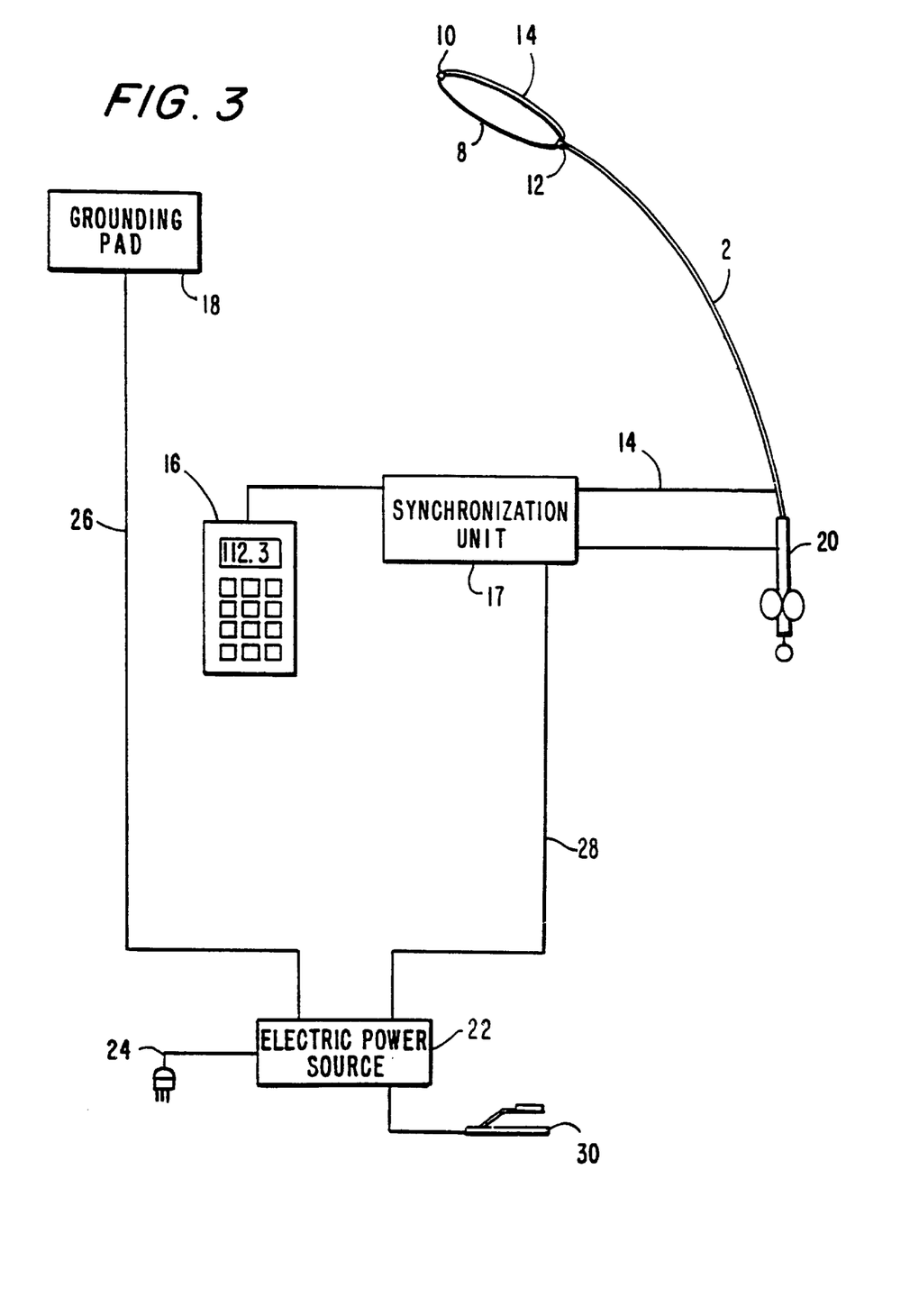
FIG. 3 depicts the temperature controlled snare of the present invention wherein the temperature-controlled snare operates in a open-loop configuration and includes an electrical power/temperature sensor synchronization component.

FIG. 3 schematically illustrates an alternative method of protecting the temperature monitor 16, and obtaining meaningful temperature data during the operation. This is achieved by insertion into the system of an electrical power/temperature measurement synchronization component 17. The synchronization unit 17 allows a periodic electrical power application with temperature measurements between every two consecutive power applications.

Figure 6:
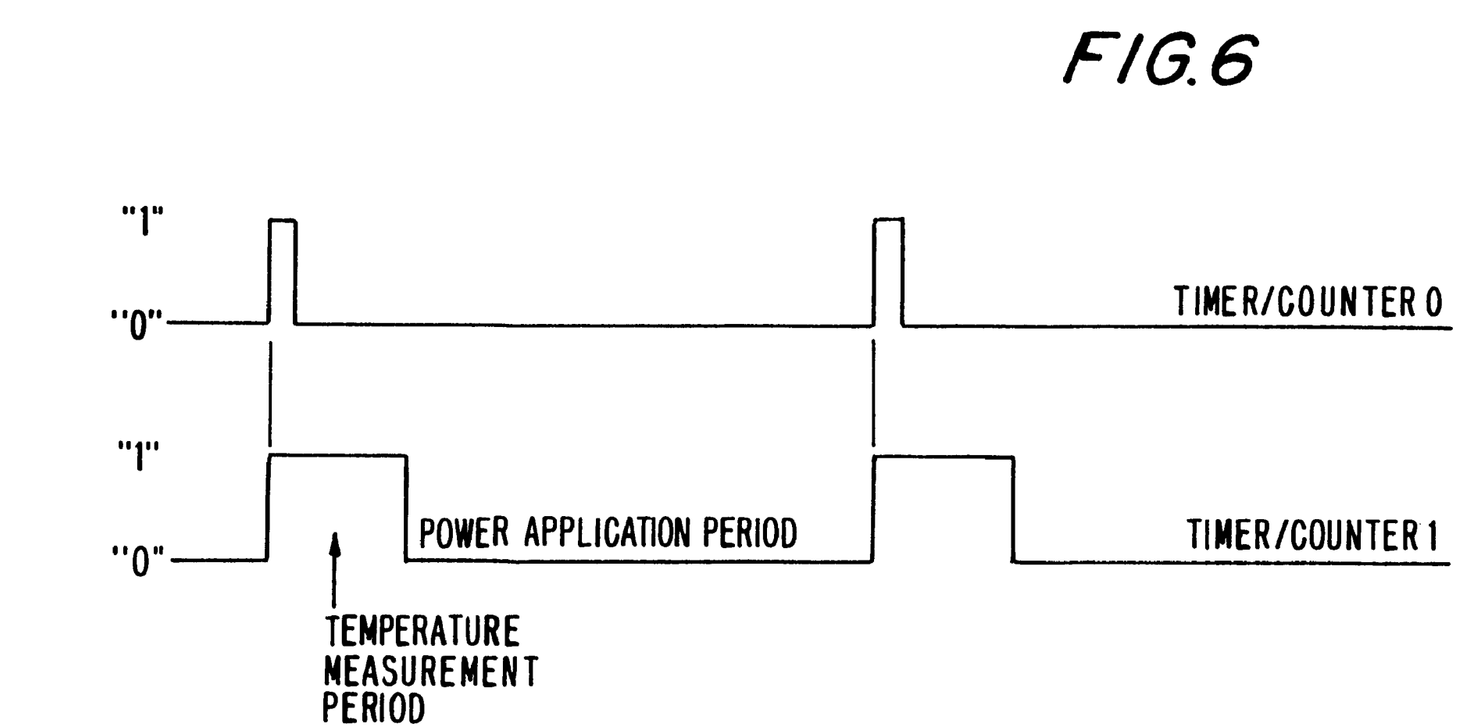
FIG. 6 is a schematic illustration of the electrical power/temperature sensor synchronization component using dual timer/counter setup.

FIG. 6 schematically illustrates one alternative of controlling this synchronization unit with two standard timer/counters. In FIG. 6, timer/counter 0 serves as the trigger for periodic temperature measurements. A typical trigger frequency may be in the range of 0.5 to 2 Hz. Timer/counter 1 opens a time window for temperature sampling, within which time period the electrical power applied to the tissue is deactivated. A typical duration of temperature sampling is up to 50 msec. The sampling time ordinarily is not longer than one tenth of the triggering period. Due to the short period temperature sampling, the effect of deactivating the applied electrical power is insignificant, and the tissue "does not feel it."

Figure 4:
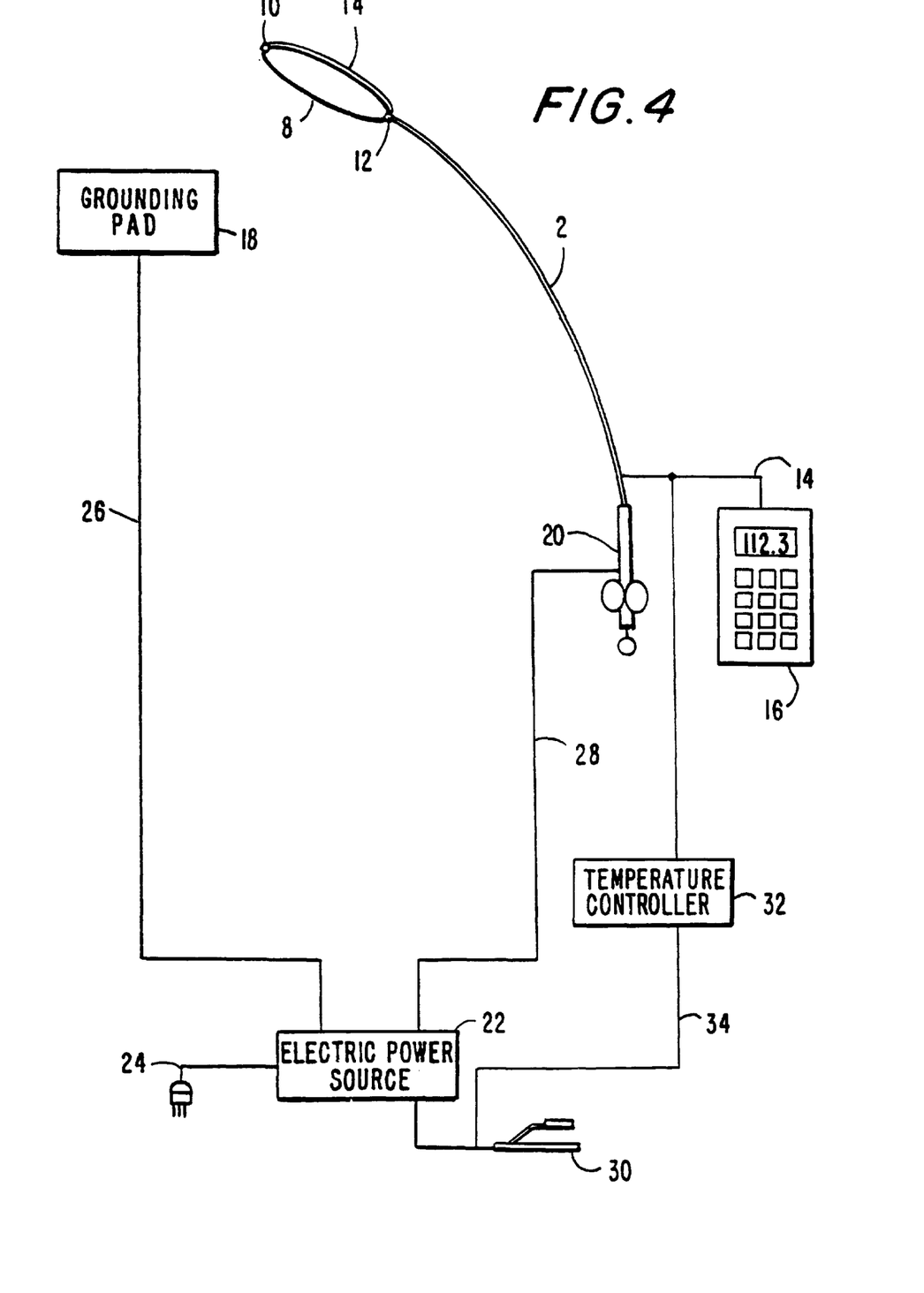
FIG. 4 depicts a third embodiment of the apparatus wherein the temperature-controlled snare operates in a closed-loop configuration with an electrical power/temperature sensor synchronization component.
Figure 5:
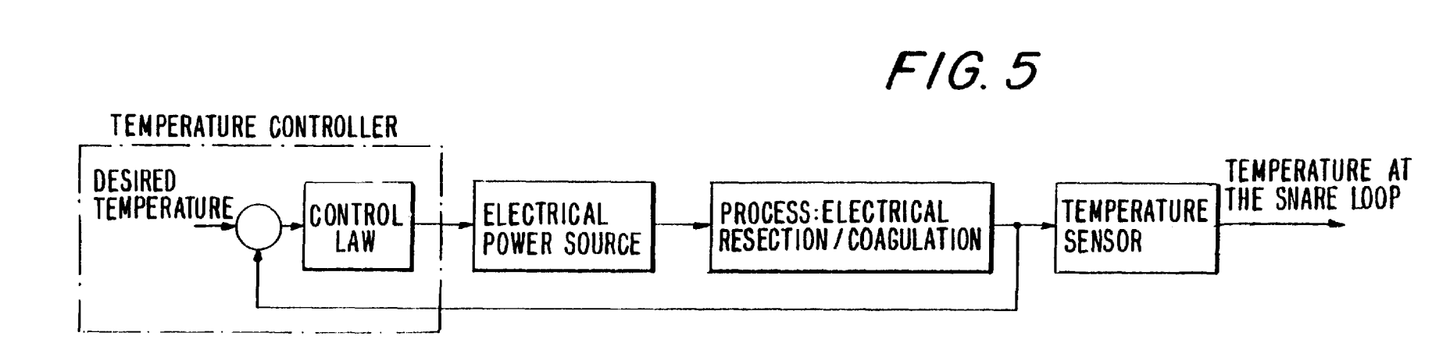
FIG. 5 is a block diagram of a temperature-controlled operation according to the present invention.

FIG. 4 schematically illustrates another embodiment of the temperature-controlled snare configuration, but in a closed-loop set-up. The closed-loop configuration of FIG. 4 is advantageous over the open-loop configuration in that a temperature controller 32 is connected to the system in order to automatically operate the electrical power source 22 without the intervention of the operator/physician. Thus, the temperature controller 32 is set to a desired and pre-specified temperature, which is accepted to be preferable for coagulation (the resection temperature). Once the temperature controller 32 is activated, it reads the temperature from the sensors 10, 12, and closes the electrical coagulation circuit whenever the sensed temperatures fall below the preselected desired temperature. Furthermore, controller 32 opens the coagulation circuit whenever the temperature rises above the upper temperature level desired for operation. Hence, temperature controller 32 controls resection for some pre-specified temperature range. Controller 32 is preferably designed as an "on-off" control, but can also be engineered as any other control such as P, PI, PID and the like. A block diagram of the self-controlled system is shown in FIG. 5. Advantageously, the temperature controller 32 should be designed to include the electrical power/temperature measurement synchronization component as a built-in circuit, as discussed above and illustrated in FIG. 6.

Closing the electrical coagulation circuit for temperature control is done via an extension cord 34 which bypasses the operation pedal 30. Bypass has the advantage of using the widely available electrical power source 22 without the necessity of any further modification.

In the open-loop configuration external monitor 16 is operative to indicate to the operator/physician when to activate and deactivate electrical coagulation. In a close-loop configuration, the temperature controller 32 is used as a safety measure to ensure an appropriate operation of the control system. The temperature controller 32 may preferably comprise a liquid crystal display (LCD) miniature monitor 16 which may be fixed by or removably assembled with the handle assembly 20 as shown in FIG. 2A. Such miniature monitor is compact and light in weight, and, therefore, does not encumber the routine operation of the handle assembly 20.

Alternatively, the temperature sensors may be connected to any standard thermometer, analog, or digital or a personal computer, to report the resection temperatures. It may also be advisable to use an electrically insulated amplifier (not shown) as another safety measure.

Temperature sensors 10, 12 may be of various types, such as, without limitation, miniature thermistors, miniature RTD's, and preferably thermocouples. Wires for the thermocouple can be lead to the point of measurement either through the same lumen as that through which the snare's metallic cable is lead, or in a separate lumen, in the case of a multi-lumen leading tube assembly. In order to save space and/or to simplify the assembly, the snare's cable can also be used as one of the two metals of the thermocouple. For example, the output of the standard copper-constantan thermocouple is similar to an unstandard thermocouple based on stainless steel and constantan. The latter thermocouple can be calibrated against the prior thermocouple, and used with standard thermometers. Both thermocouple materials are very suitable for the temperature range of electrical coagulation.

Additional advantages and modifications will readily occur to those skilled in the art. Therefore, the invention in its broader aspects is not limited to the specific details, and representative configurations shown and described herein. Accordingly, various modifications may be made without departing from the spirit and scope of the general inventive concept as defined by the appended claims and their equivalents.

What is claimed is:

1. An apparatus for polyp removal comprising:
   (i) an endoscopic guide tube;
   (ii) a heating element;
   (iii) an electrical power source;
   (iv) a power transmitting element traversing through said guide tube and communicating with said heating element;
   (v) a temperature sensor provided on the outside surface of said heating element measuring temperature of the polyp to be applied during polypectomy; and
   (vi) a temperature controlling element for receiving temperature information from said sensor relating to the temperature of the polyp and then signaling said power source to supply power to said heating element to heat the polyp to a pre-determined temperature to avoid excessive bleeding during resection of the polyp, said temperature controlling element turning off said power supply if said temperature sensor senses a temperature greater than said pre-determined temperature and turning on said power supply if said sensor senses a temperature less than said pre-determined temperature, said temperature controlling element turning off and turning on said power supply in a periodic manner until the resection is complete.

2. The apparatus according to claim 1 further comprising an electrical power supply and temperature measurement synchronization component to prevent interference between power application and temperature readings.

3. The apparatus according to claim 1 wherein said heating element is an electrically heated snare loop sufficient in size to surround the polyp.

4. The apparatus according to claim 3 wherein said sensor is positioned at least along one portion of said snare loop.

5. The apparatus according to claim 4 wherein said sensor has a first and second sensor unit each adjoining said loop at positions on the loop approximately equidistant from one another.

6. The apparatus according to claim 1 wherein the signaling to said power source for adjusting the temperature occurs automatically through a programmed controller.

7. The apparatus according to claim 1 wherein adjustment of the temperature occurs over a temperature range from about 50° C. to about 300° C.

8. The apparatus according to claim 1 wherein adjustment of the temperature occurs at a preselected heating rate.

9. The apparatus according to claim 1 further comprising a temperature monitor operatively connected to said temperature sensor.

10. The apparatus according to claim 9 further including a handle mounting said endoscopic guide tube.

11. The apparatus according to claim 10 wherein said temperature monitor is mounted on said handle.

12. A method for performing a polypectomy comprising:
   (A) providing an endoscopic kit comprising:
      (i) an endoscopic guide tube;
      (ii) a heating element;
      (iii) a power transmitting element traversing through the guide tube and communicating with said heating element;
      (vi) a temperature sensor provided on the outside surface of said heating element for measuring temperature of the polyp; and
      (v) a temperature controlling element for receiving temperature information from said sensor and then signaling a power source for adjusting the temperature of said heating element to a pre-determined temperature;

(B) inserting said endoscopic guide tube into a human body;

(C) deploying said heating element to surround a polyp;

(D) sensing the temperature of the polyp;

(E) energizing said heating element to begin a resection of the polyp;

(F) turning off said power supply to de-energize said heating element if said temperature sensor senses a temperature greater than a pre-determined temperature to avoid excessive bleeding during the resection;

(G) turning on said power supply to re-energize said heating element if said temperature sensor senses a temperature less than said pre-determined temperature; and (H) repeating steps (F) and (G) until the resection is completed.

13. A kit for performing a polypectomy comprising:

(I) an apparatus comprising:
   (i) an endoscopic guide tube;
   (ii) a heating element;
   (iii) a power transmitting element traversing through the guide tube and communicating with the heating element;
   (iv) at least one temperature sensor provided on the outside surface of said heating element for measuring temperature of the polyp; and
   (v) a temperature controlling element for receiving temperature information from said sensor relating to the temperature of the polyp and then signaling said power source to supply power to said heating element to heat the polyp to a pre-determined temperature to avoid excessive bleeding during resection of the polyp, said temperature controlling element turning off said power supply if said temperature sensor senses a temperature greater than said pre-determined temperature and turning on said power supply if said sensor senses a temperature less than said pre-determined temperature, said temperature controlling element turning off and turning on said power supply in a periodic manner until the resection is complete;

(II) written instructions instructing a practitioner of the operation of said apparatus.

14. The apparatus according to claim 1 wherein a human operator activates and controls said heating element in order to maintain the temperature of said heating element at said pre-determined temperature throughout polyp removal, the human operator controlling the temperature by changing the amount of power supplied to said heating element, in accordance with temperature data sensed by said temperature sensor.

15. The method in accordance with claim 12, further including the step of automatically adjusting said power source based upon information supplied by said temperature sensor.

16. The method accordance with claim 15, further including the step of automatically adjusting said power source at a pre-selected heating rate.

* * * * *